(12) United States Patent
Sekiya et al.

(10) Patent No.: US 7,041,317 B2
(45) Date of Patent: May 9, 2006

(54) SUSTAINED-RELEASE PREPARATION CONTAINING 5-ACETYL-4,6-DIMETHYL-2 [2-[4-(2-METHOXYPHENYL) PIPERAZINYL]ETHYLAMINO] PYRIMIDINE TRIHYDROCHLORIDE AS ACTIVE INGREDIENT

(75) Inventors: Noboru Sekiya, Mishima-gun (JP); Yoshinori Ii, Mishima-gun (JP); Masayuki Ishikawa, Setagaya-ku (JP); Hiroshi Azuma, Kuki (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 532 days.

(21) Appl. No.: 10/399,686

(22) PCT Filed: Oct. 22, 2001

(86) PCT No.: PCT/JP01/09241

§ 371 (c)(1),
(2), (4) Date: Apr. 22, 2003

(87) PCT Pub. No.: WO02/34268

PCT Pub. Date: Feb. 5, 2002

(65) Prior Publication Data

US 2005/0101606 A1    May 12, 2005

(30) Foreign Application Priority Data

Oct. 23, 2000  (JP) ............................. 2000-322825

(51) Int. Cl.
*A61K 9/22* (2006.01)
*A61K 9/20* (2006.01)

(52) U.S. Cl. ...................... 424/468; 424/464; 514/964

(58) Field of Classification Search ................ 424/468, 424/464
See application file for complete search history.

(56) References Cited

U.S. PATENT DOCUMENTS 5,075,308 A    12/1991    Ishikawa et al.

FOREIGN PATENT DOCUMENTS

| JP | 62-51672 A | 3/1987 |
| JP | 8-73345 A | 3/1996 |
| WO | WO 88/07369 A1 | 10/1988 |
| WO | WO 90/14077 A1 | 11/1990 |

OTHER PUBLICATIONS

Hiroshi Azuma et al., "$\alpha_1$-Adrenoceptor antagonist activity of novel pyrimidine derivatives (SH1437 and IK29) in rabbit aorta and trigone of the bladder" (1989) British Journal of Pharmacology 1989 United Kingdom vol. 96, No. 4, pp. 1000-1006.

Supplementary European Search Report dated Jul. 19,2005.

*Primary Examiner*—Thurman K. Page
*Assistant Examiner*—Marc C. Fitzgerald
(74) *Attorney, Agent, or Firm*—Sughrue Mion, PLLC

(57) ABSTRACT

A sustained-release formulation of 5-acetyl-4,6-dimethyl-2-[2-[4-(2-methoxyphenyl)piperazinyl]ethylamino]pyrimidine trihydrochloride coated with a release-controlling film comprising a water-insoluble polymer film having no hydrophilic group. The formulation of the present invention has such a release pattern that the drug release lasts for 20 hours or more, so that can be appropriately administered for treatment. Furthermore, the formulation itself is so stable that its release pattern does not change with pH and the formulation does not suffer from deterioration, coloration and the like with the lapse of time.

5 Claims, 5 Drawing Sheets

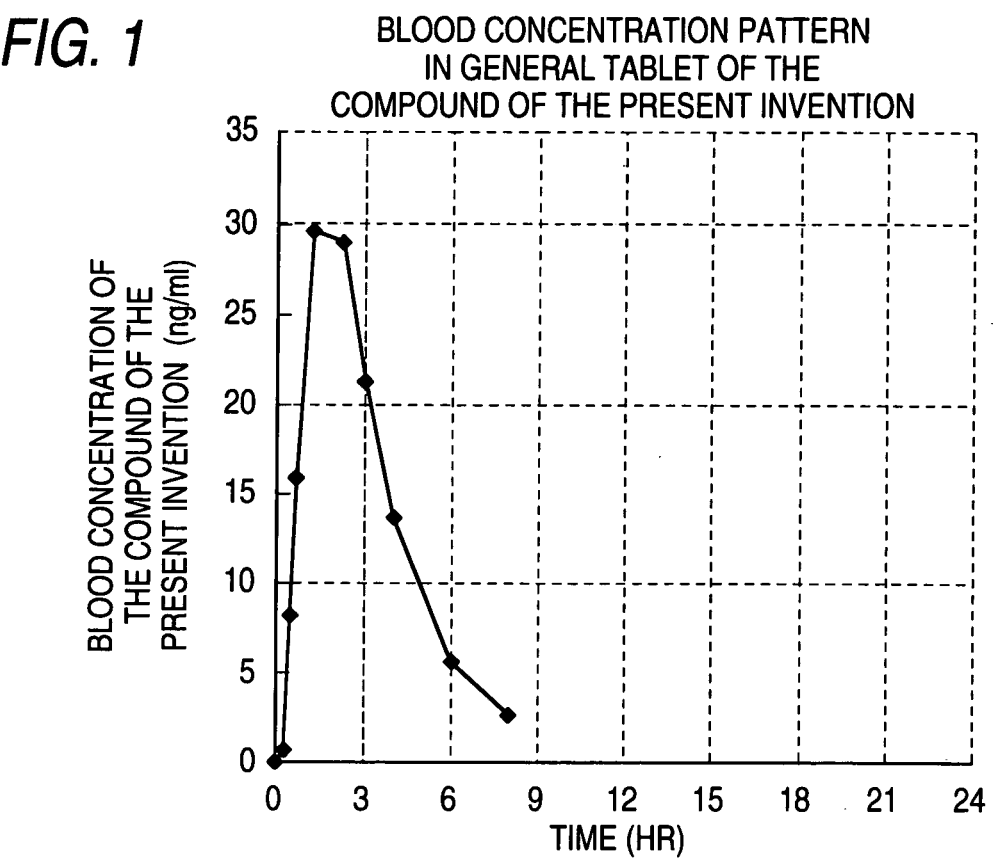
FIG. 1 BLOOD CONCENTRATION PATTERN IN GENERAL TABLET OF THE COMPOUND OF THE PRESENT INVENTION
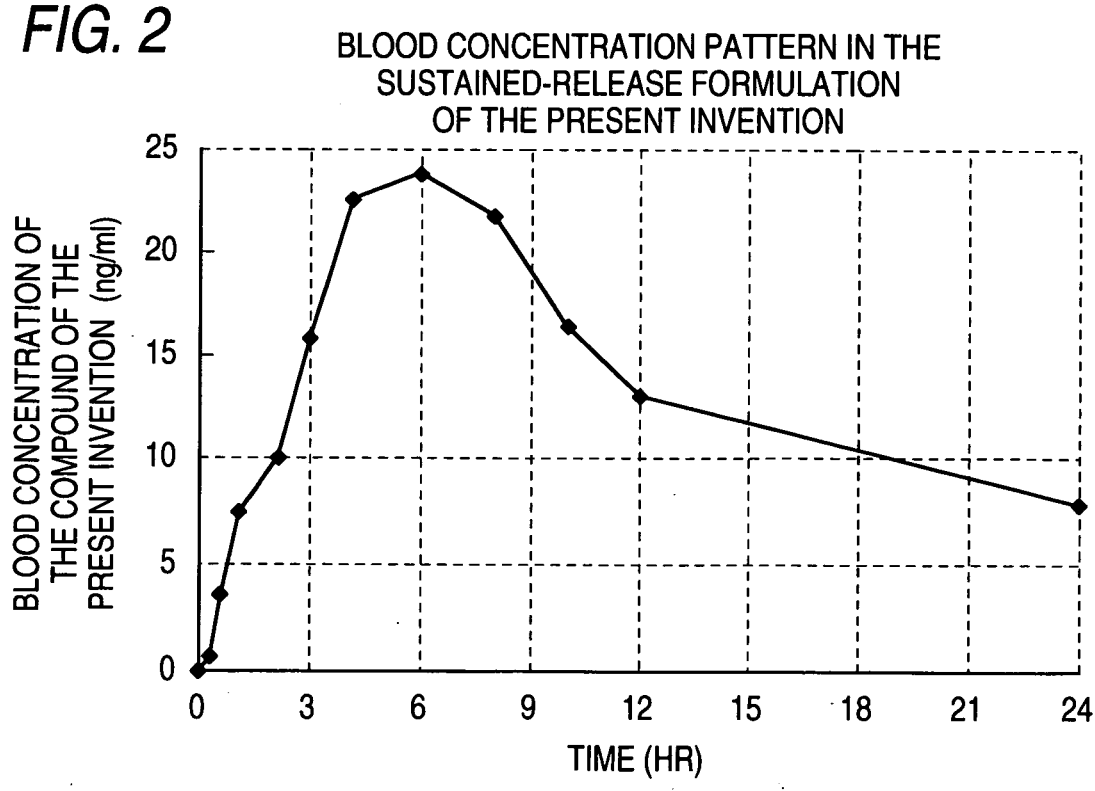
FIG. 2 BLOOD CONCENTRATION PATTERN IN THE SUSTAINED-RELEASE FORMULATION OF THE PRESENT INVENTION

SUSTAINED-RELEASE PREPARATION CONTAINING 5-ACETYL-4,6-DIMETHYL-2 [2-[4-(2-METHOXYPHENYL) PIPERAZINYL]ETHYLAMINO] PYRIMIDINE TRIHYDROCHLORIDE AS ACTIVE INGREDIENT

TECHNICAL FIELD

The present invention relates to sustained-release formulations of 5-acetyl-4,6-dimethyl-2-[2-[4-(2-methoxyphenyl)piperazinyl]ethylamino]pyrimidine trihydrochloride.

BACKGROUND OF THE INVENTION

5-Acetyl-4,6-dimethyl-2-[2-[4-(2-methoxyphenyl)piperazinyl]ethylamino]pyrimidine trihydrochloride represented by the following structural formula:

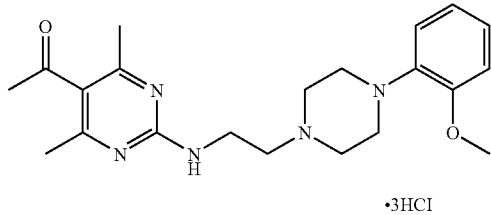

·3HCl (hereinafter referred to as the compound of the present invention) has an α-blocker activity and is useful as a therapeutic agent for urinary disturbance (JP-A-62-51672, JP-A-3-90027 (U.S. Pat. No. 5,075,308)).

Although the compound of the present invention is stable, it has a property of being quick in both absorption and metabolism, so that its effective blood concentration cannot be maintained for a prolonged period of time. That is, as shown in FIG. 1 regarding the blood concentration pattern when a conventional tablet (the tablet produced in Comparative Example 1 which is described later containing 3 mg of the compound of the present invention) is orally administered, the effective blood concentration can be maintained for merely about 5 hours. Accordingly, it is necessary to administer the compound of the present invention repeatedly at relatively small doses in order to keep its activity and effect as an α-blocker.

In order to solve the problem, the present inventors have made an attempt to make the compound of the present invention into a sustained-release formulation.

When a sustained-release formulation is prepared, it is generally carried out to coat the periphery of a granule or a tablet with a sustained release film. The inventors also have examined on this technique in various manners and verified as a result that a drug can be released continuously for 12 hours or more by sustained-release formulations using ethyl cellulose and an ethyl acrylate-methyl methacrylate-ethyl trimethylammoniumchloride methacrylate copolymer (Eudragit RS30D, trade name, Rohm Pharma) as the release controlling membranes. However, each formulation could not show a constant releasing pattern due to great influence of pH on the dissolution rate and was lacking in stability due to periodical coloring.

Based on an assumption that the compound of the present invention of being hydrochloride would be the cause of the unstable releasing pattern and periodical unstableness of the above formulations, the inventors have conducted intensive studies on sustained-release formulations using those films which are not influenced by acid, namely water-insoluble films having no hydrophilic group, as the sustained release films. As a result, formulations capable of keeping their activities and effects and showing a constant releasing pattern and also having periodical stability were obtained, thereby resulting in the accomplishment of the present invention.

DISCLOSURE OF THE INVENTION

Accordingly, the present invention relates to sustained-release formulations of the following 1 to 5.

1. A sustained-release formulation of 5-acetyl-4,6-dimethyl-2-[2-[4-(2-methoxyphenyl)piperazinyl]ethylamino]pyrimidine trihydrochloride coated with a release-controlling film comprising a water-insoluble polymer film having no hydrophilic group.

2. The sustained-release formulation of 5-acetyl-4,6-dimethyl-2-[2-[4-(2-methoxyphenyl)piperazinyl]ethylamino]pyrimidine trihydrochloride according to the above item 1, wherein the water-insoluble polymer film having no hydrophilic group is a copolymer of ethyl acrylate with methyl methacrylate.

3. The sustained-release formulation of 5-acetyl-4,6-dimethyl-2-[2-[4-(2-methoxyphenyl)piperazinyl]ethylamino]pyrimidine trihydrochloride according to the above item 2, wherein the copolymer of ethyl acrylate with methyl methacrylate has a ratio of ethyl acrylate:methyl methacrylate=1 to 4:1.

4. The sustained-release formulation of 5-acetyl-4,6-dimethyl-2-[2-[4-(2-methoxyphenyl)piperazinyl]ethylamino]pyrimidine trihydrochloride according to the above item 2, wherein the copolymer of ethyl acrylate with methyl methacrylate has a ratio of ethyl acrylate:methyl methacrylate=1.5 to 3.5:1.

5. The sustained-release formulation of 5-acetyl-4,6-dimethyl-2-[2-[4-(2-methoxyphenyl)piperazinyl]ethylamino]pyrimidine trihydrochloride according to the above item 2, wherein the copolymer of ethyl acrylate with methyl methacrylate is an ethyl acrylate-methyl methacrylate copolymer emulsion.

According to the sustained-release formulations of the present invention, formulations having an appropriate releasing pattern can be obtained, and administration suitable for treatments can be carried out. Also, these sustained-release formulations are stable and do not cause periodical deterioration, coloring and the like. That is, as shown in FIG. 2 regarding changes in human blood concentration when the sustained-release formulation of the present invention (9 mg of the compound of the present invention) is used, the effective blood concentration is maintained for about 20 hours.

DETAILED DESCRIPTION OF THE INVENTION

The formulation of the present invention is explained below in detail.

Each of the sustained-release formulations of the present invention comprises drug particles and a release-controlling film.

Drug Particles:

The drug particles comprise the compound of the present invention, an excipient, a fluidizing agent, a binder and the like and are prepared by grinding, mixing and granulating.

The filler includes cornstarch and the like. The fluidizing agent includes soft silicic anhydride and the like. The binder includes hydroxypropylcellulose and the like.

In the granulation, a core material may not be used, but is preferably used in view of sphericity, release pattern stability and the like. The core material includes sucrose and cellulose.

Mixing ratios of a filler and the like to the compound of the present invention in the drug particles are, for example, approximately from 300 to 700 g of the excipient and from 3 to 30 g of the fluidizing agent, based on 100 g of the compound of the present invention, and up to about 2,500 g of the core material can be used.

Release Controlling Film:

The release-controlling film used in the sustained-release formulation of the present invention is not particularly limited, so long as it is a film comprising a pharmacologically acceptable water-insoluble polymer having no hydrophilic group. In this case, the hydrophilic group includes groups which are compatible with water such as a hydroxy group, an amino group and a carboxy group. They may be either ionic or nonionic.

A preferable material used as the release-controlling film in the present invention includes a copolymer of ethyl acrylate with methyl methacrylate.

In a more preferable release controlling material, the ratio of ethyl acrylate to methyl methacrylate is from 1 to 4 of ethyl acrylate based on 1 of methyl methacrylate. The ratio is more preferably from 1.5 to 3.5 of ethyl acrylate based on 1 of methyl methacrylate.

The most preferable release-controlling film is a copolymer of ethyl acrylate with methyl methacrylate having a ratio of ethyl acrylate: methyl methacrylate=7:3. Specific examples include an ethyl acrylate-methyl methacrylate copolymer emulsion (Eudragit NE30D (trade name, manufactured by Rohm Pharma)). Eudragit NE30D is an emulsion of a copolymer obtained in an aqueous polyoxyethylene nonylphenyl ether (100 E.O.) solution of ethyl acrylate and methyl methacrylate, and dried formulation of this product contains from 7.0 to 10.0% of a methoxy group and from 21.0 to 33.0% of an ethoxy group.

Method for the Preparation of the Formulation of the Present Invention

The sustained-release formulation of the present invention can be produced, for example, by the following method.

1. A mixture of a ground drug substance (the compound of the present invention), an excipient and a fluidizing agent is prepared.
2. A mixture of a binder and a solvent (e.g., water, ethanol, etc.) is prepared.
3. The preparations of 1 and 2 are mixed and granulated. In this case, a material used as the core may be simultaneously mixed.
4. Thus obtained particles are dried.
5. A water-insoluble polymer having no hydrophilic group is mixed with an adhesion preventing agent (e.g., talc, etc.) and a solvent (e.g., water, etc.), and the dried particles of 4 are coated using thus obtained emulsion and a fluidizing agent (e.g., soft silicic anhydride, etc.).
6. The release-controlling film on each particle is subjected to curing by keeping it at a temperature of from 50 to 100° C., preferably from 60 to 80° C., for 30 minutes to 12 hours, preferably 1 to 8 hours.

It is preferable to coat the release-controlling film in such an amount that is approximately from 10 to 14% by weight of the drug particle after curing.

A partially cutaway perspective view of a particle of the formulation of the present invention, prepared by coating a drug layer (2) of the compound of the present invention with the release-controlling film (3) of the present invention using a granulation core material (1), is shown in FIG. 9 as a preferred embodiment of the present invention.

By granulating by the above method, a particle preparation having an average particle diameter of from 0.1 mm to several mm, preferably about 1 mm, is obtained. This particle preparation can be used directly as granules or made into a final product by packing into capsules.

BRIEF DESCRIPTION OF THE DRAWINGS

FIG. 1 shows a pattern of a blood drug concentration when a general tablet of the compound of the present invention is administered to human.

FIG. 2 shows a pattern of a blood drug concentration when the sustained-release formulation of the present invention is administered to human.

BEST MODE FOR CARRYING OUT THE INVENTION

Figure 3:
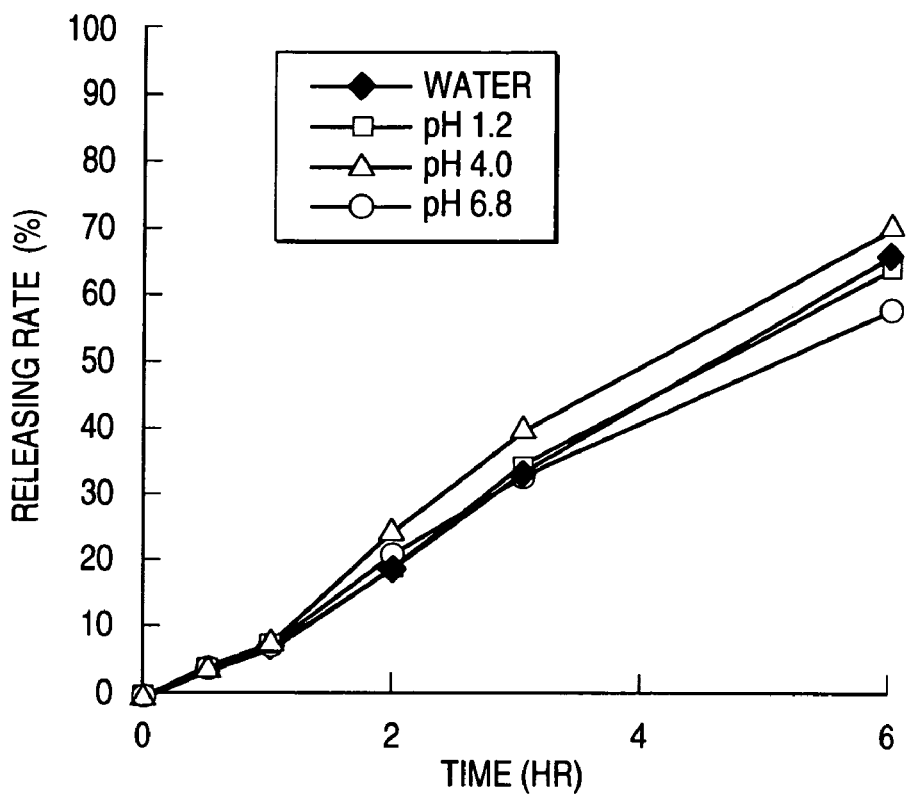
FIG. 3 shows a releasing pattern of the formulation of the present invention at various pH values.

The present invention is described below with reference to Examples and Comparative Examples, but the present invention is not limited thereto.

EXAMPLE 1

Production of the Sustained-release Formulation of the Present Invention

The compound of the present invention (drug substance, 30 g), cornstarch (187.5 g) and soft silicic anhydride (1 g) were mixed. Using crystalline cellulose particles (700 g, particle diameter 0.5 to 0.7 mm) as the core particles, the mixture was coated with an ethanol (376 g) solution of hydroxypropylcellulose (24 g) as a binder and then granulated. The granulated product was dried using a fluidized bed dryer and then classified.

Thus obtained drug particles (average particle diameter 600 to 700 μm, 400 g) were coated with talc (24 g) and an aqueous suspension of Eudragit NE30D (trade name; Rohm Pharma, 80 g, 24 g as a solid content). When application of the predetermined coating solution was completed, a fluidizing agent was added thereto and curing was carried out at 70° C. for 6 hours. Thus obtained granules were packed in gelatin capsules in such an amount that each capsule contain 3 mg of the compound of the present invention.

EXAMPLE 2

Large Scale Production of the Sustained-Release Formulation of the Present Invention About 50 kg of drug particles were obtained in the same manner as in Example 1 (production method of drug particles), except that amounts of the raw materials in Example 1 were changed to the compound of the present invention (drug substance, 1.6 kg), cornstarch (9.8 kg), soft silicic anhydride (60 g), crystalline cellulose particles (37 kg, particle diameter 0.5 to 0.7 mm), hydroxypropylcellulose (1.705 kg) and ethanol solution (18.3 kg).

The above operation was repeated twice, and the sustained-release formulation of the present invention was obtained from thus obtained drug particles (average particle diameter 600 to 700 μm, 95 kg) in the same manner as in Example 1 (production method of drug controlling layer) using talc (5.7 kg) and an aqueous suspension of Eudragit NE30D (trade name; Rohm Pharma, 19 kg, 5.7 kg as a solid content).

Figure 4:
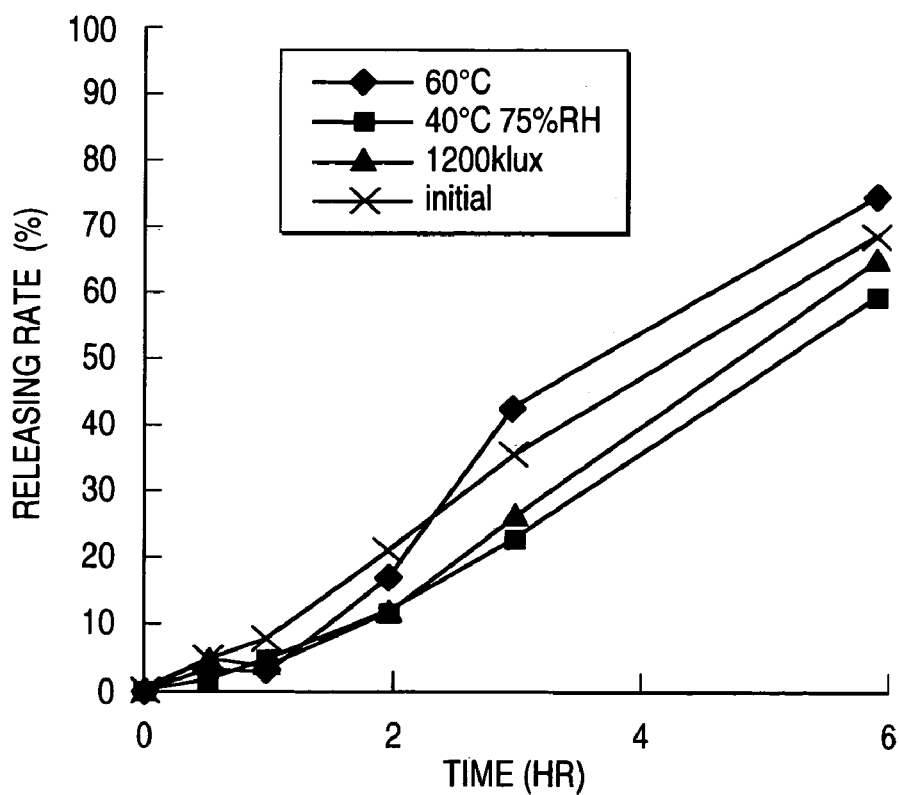
FIG. 4 shows a releasing pattern of the formulation of the present invention after an acceleration test.

Dissolution Test:

The dissolution test was carried out in accordance with the 100 rpm paddle method of Japanese Pharmacopoeia. Buffer solutions having various pH values imitating human digestive organs were used as the eluent. The results are shown in FIG. 3. Also, the formulation of the present invention was subjected to (1) a heating test at 60° C., (2) a 75% humidification test at 40° C. and (3) an acceleration test of 1,200 klux light exposure, each for 2 months, and then the dissolution test was carried out in the same manner to evaluate its stability. Purified water was used as the eluent. The results are shown in FIG. 4. The "initial" in the drawing means the formulation of the present invention without treatment.

Results:

In the paddle method dissolution test of Japanese Pharmacopoeia, it showed a similar releasing pattern at each pH, so that changes in pattern by pH were not observed.

Regarding the results of dissolution tests after heating, humidification and light exposure test (FIG. 4), the formulation after each acceleration test showed no significant changes in comparison with the "initial" so that there was no problem in terms of stability. In addition, coloring in appearance was not observed, either.

COMPARATIVE EXAMPLE 1

Production of General Tablets

The compound of the present invention (drug substance, 30 g) was mixed with mannitol (577 g), crystalline cellulose (300 g), low substitution hydroxypropylcellulose (50 g) and soft silicic anhydride (5 g), and the mixture was granulated using a fluidized bed granulator by spraying an aqueous hydroxypropylcellulose (30 g) solution. After completion of the granulation, the granules were dried, mixed with magnesium stearate and then made into tablets to obtain un-coated tablets. By coating thus obtained un-coated tablets with a coating solution prepared by adding water to hydroxypropylmethylcellulose (9 g), macrogol 6000 (0.9 g) and titanium oxide (3 g) to a total volume of 90 g, tablets (10,000 tablets) each containing 3 mg of the compound of the present invention were obtained.

Figure 5:
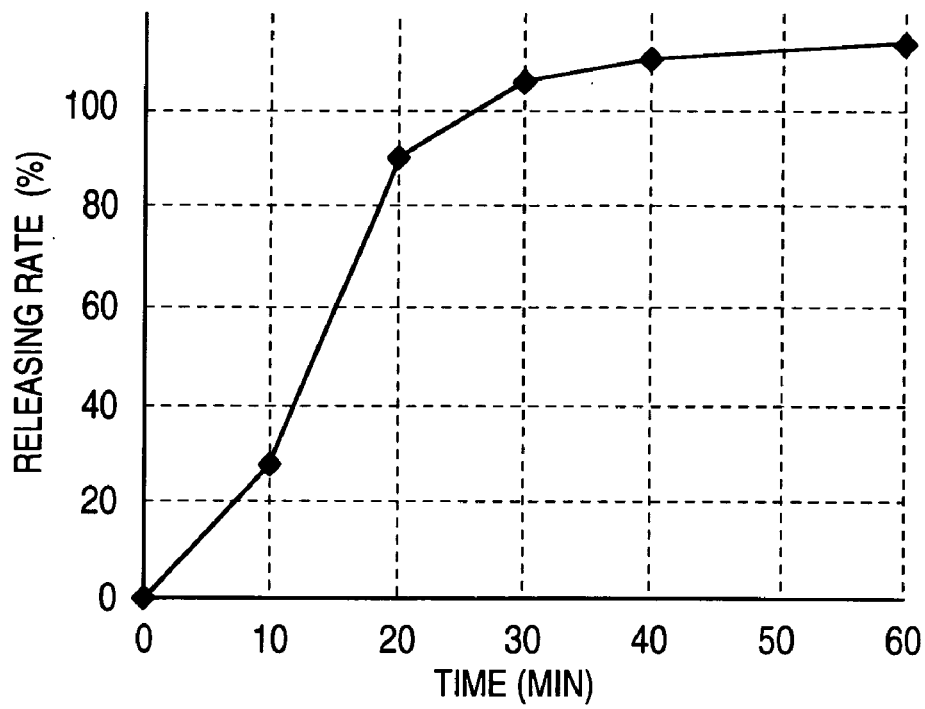
FIG. 5 shows a releasing pattern of a general tablet of the compound of the present invention.

Dissolution Test:

The dissolution test was carried out using the 50 rpm paddle method of Japanese Pharmacopoeia. Purified water was used as the eluent. The results are shown in FIG. 5. Since they showed a releasing ratio of 75% or more in 30 minutes, it was concluded that it was impossible to use them as a pharmaceutical formulation.

COMPARATIVE EXAMPLE 2

Sustained Release Formulation Using Ethyl Cellulose

The compound of the present invention (drug substance, 30 g), cornstarch (187.5 g) and soft silicic anhydride (1 g) were mixed. Using crystalline cellulose particles (700 g) as the core particles, the mixture was coated with an ethanol (376 g) solution of hydroxypropylcellulose (24 g) as a binder and then granulated. The granulated product was dried using a fluidized bed dryer and then classified.

Thus obtained drug particles (400 g) were coated with ethyl glycerol fatty acid (15.6 g), hydroxypropylmethylcellulose (TC5EW; trade name, manufactured by Shin-Etsu Chemical) (1.6 g) and ethyl cellulose (Aquacoat; trade name; Asahi Chemical Industry) (109.2 g, 62.8 g as a solid content). When the predetermined coating solution was completely applied, curing was carried out. Thus obtained granules were packed in gelatin capsules in such an amount that each capsule contain 3 mg of the compound of the present invention.

Figure 6:
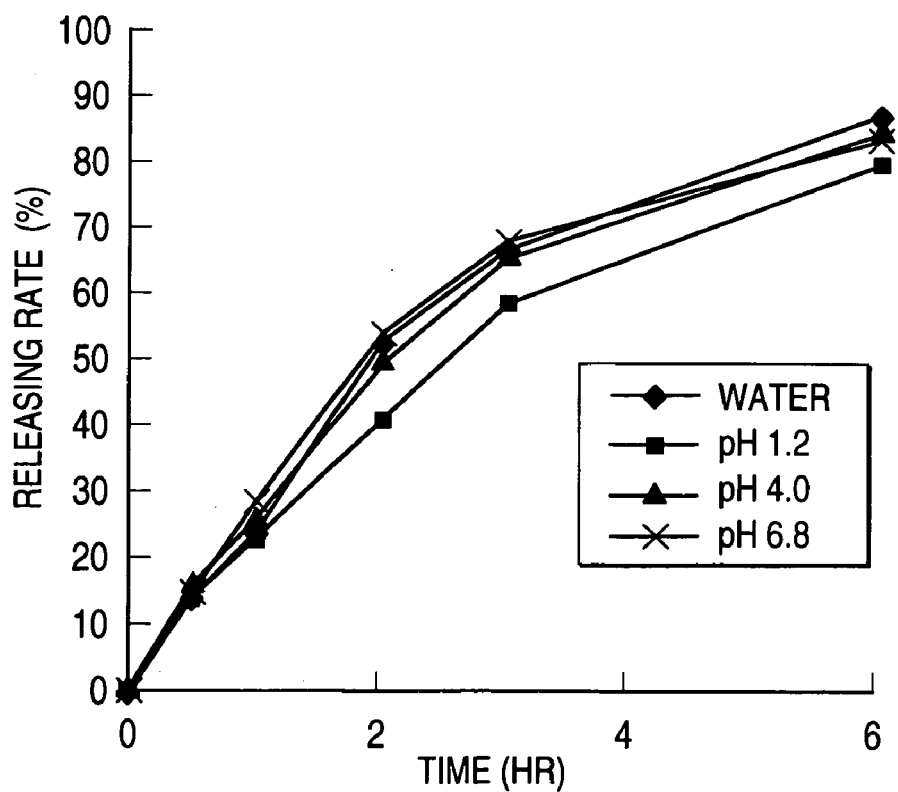
FIG. 6 shows a releasing pattern of a sustained-release formulation of the compound of the present invention by an ethyl cellulose film at various pH values.
Figure 7:
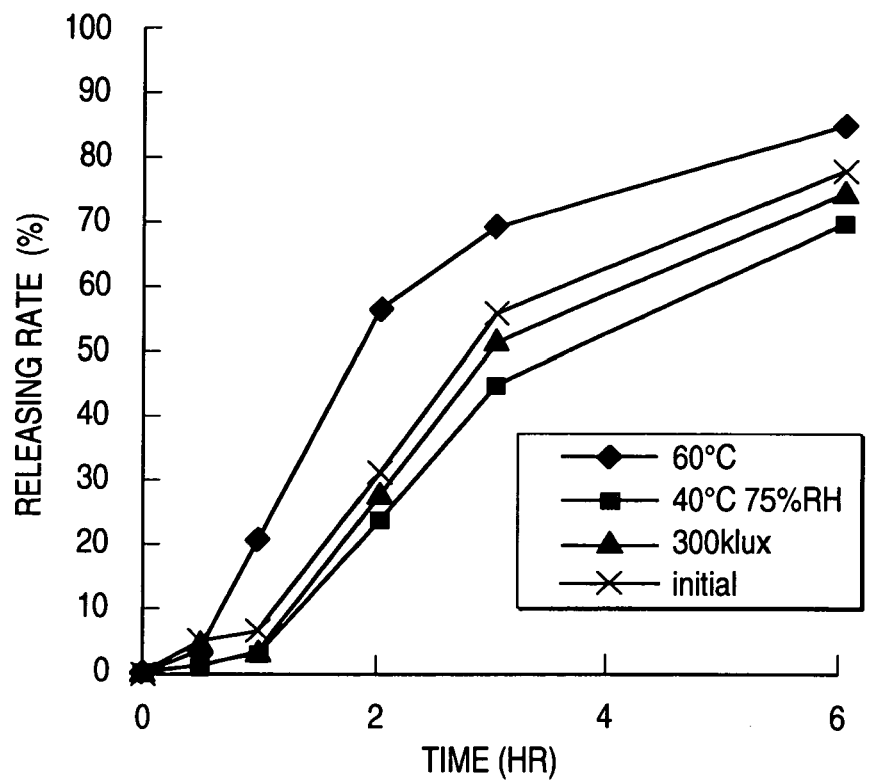
FIG. 7 shows a releasing pattern of a sustained-release formulation of the compound of the present invention by an ethyl cellulose film after an acceleration test.

Dissolution Test:

The dissolution test was carried out in the same manner as in Example 1, in accordance with the 100 rpm paddle method of Japanese Pharmacopoeia. Purified water was used as the eluent. Also, a stability test was carried out in the same manner as in Example 1. However, the light exposure was carried out at 300 klux instead of 1200 klux. The results are shown in FIG. 6 (paddle method dissolution test of Japanese Pharmacopoeia) and FIG. 7 (stability test). As a result of dissolution test, difference in dissolution by pH was not found. After the heating, humidification and light exposure acceleration tests (stability test), light brown discoloration was observed with the naked eye under all conditions. As shown in FIG. 7, the dissolution rate was significantly quick in the formulation after the 60° C. heating test, among the acceleration tests, and its periodical change was observed.

COMPARATIVE EXAMPLE 3

Sustained Release Formulation Using Eudragit RS30D (Trade Name)

The compound of the present invention (drug substance, 30 g), cornstarch (187.5 g) and soft silicic anhydride (1 g) were mixed. Using crystalline cellulose particles (700 g) as the core particles, the mixture was coated with an ethanol (376 g) solution of hydroxypropylcellulose (24 g) as a binder and then granulated. The granulated product was dried using a fluidized bed dryer and then classified.

Thus obtained drug particles (400 g) were coated with talc (16.2 g), triethyl citrate (3.25 g) and an aqueous suspension of Eudragit RS30D (an ethyl acrylate-methyl methacrylate-ethyl trimethylammoniumchloride methacrylate copolymer) (trade name; Rohm Pharma) (108 g, 32.5 g as a solid content). When application of the predetermined coating solution was completed, curing was carried out. Thus obtained granules were packed in gelatin capsules in such an amount that the compound of the present invention content became 3 mg per capsule.

Figure 8:
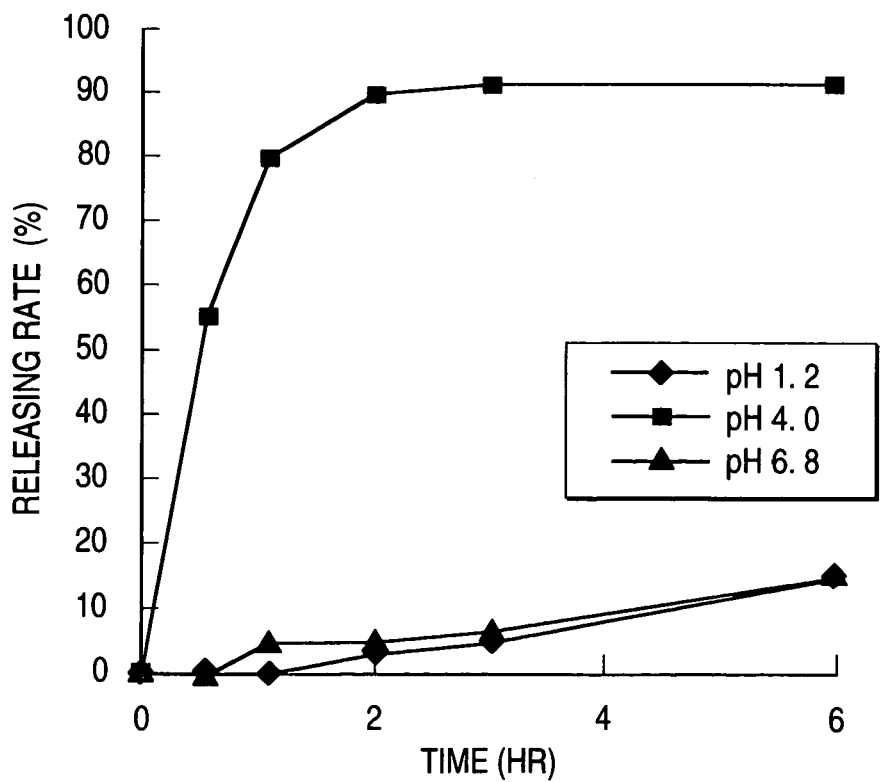
FIG. 8 shows a releasing pattern of a sustained-release formulation of the compound of the present invention by an Eudragit RS30D film at various pH values.
Figure 9:
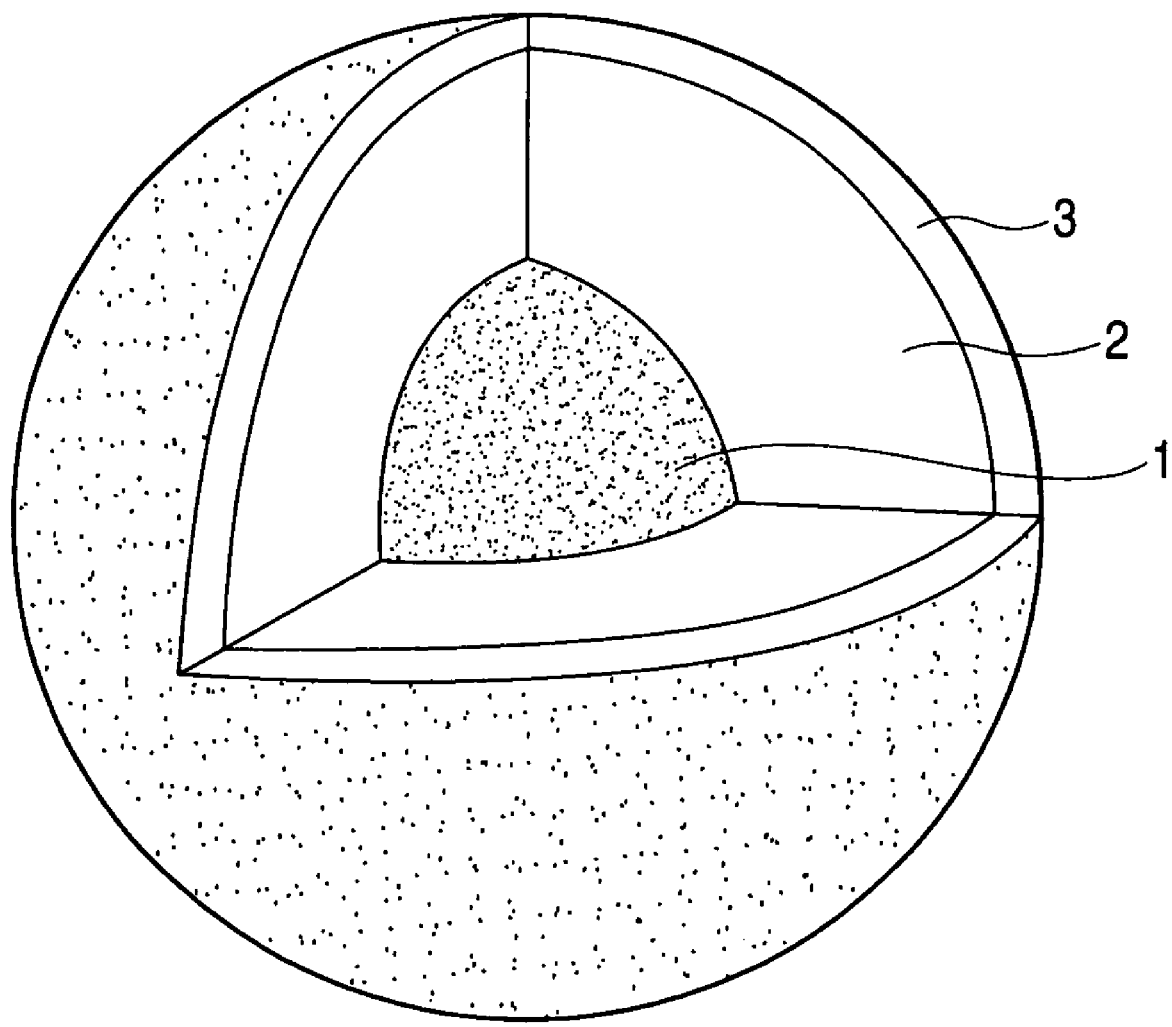
FIG. 9 is a partially cutaway perspective view of a preferred embodiment of the sustained-release formulation of the present invention.

Dissolution Test:

The dissolution test was carried out using the 100 rpm paddle method of Japanese Pharmacopoeia, similar to the case of Example 1. Purified water was used as the eluent. The results are shown in FIG. 8. A great difference in the dissolution rate by pH was found. The dissolution was markedly slow at pH 1.2 and pH 6.8 but the dissolution was quick at pH 4.0, thus finding that a stable release cannot be obtained when administered to human. Although it is reported that the Eudragit RS is not influenced by pH, it is apparent that it is influenced by pH in the case of the formulation of the compound of the present invention.

Results of Example 1 and Comparative Examples 1 to 3 are shown in Table 1.

TABLE 1

|  | Releasing pattern | Stability | Coloring |
| --- | --- | --- | --- |
| Sustained release formulation of the present invention | Period necessary for 50% release is 4 hours (good) | No changes in the releasing pattern after 60 days at 60° C. and after 60 days at 40° C. in 75% RH. | No |
| General tablets (Comp. Ex. 1) | Cannot be used due to 75% or more of dissolution in 30 min. | Stable | No |
| Sustained release formulation using ethyl cellulose (Comp. Ex. 2) | Period necessary for 50% release is 2 hours (good) | Releasing ratio becomes quick after 60 days at 60° C., and periodical changes are observed. | Light brown coloring during storage |
| Sustained release formulation using Eudragit RS30D (Comp. Ex. 3) | 5% or less at pH 1.2 and 6.8 after 2 hours, and 90% at pH 4.0 after 2 hours (influence by pH) | Not measured | Light brown coloring during storage |

As shown in Table 1, general tablets cannot be used due to too quick release. The sustained-release formulation which used Eudragit RS30D cannot be used, because its releasing pattern changes due to influence of pH and it develops color during storage. Although the sustained-release formulation which used ethyl cellulose has no problem regarding its releasing pattern, it has problems in terms of periodical changes by temperature and coloring during storage.

On the other hand, it can be seen that the sustained-release formulation of the present invention is an excellent formulation, because it shows a proper releasing pattern, the releasing pattern is not changed by pH and it does not cause coloring during storage.

The invention claimed is:

1. A sustained-release formulation of 5-acetyl-4,6-dimethyl-2-[2-[4-(2-methoxyphenyl)piperazinyl]ethylamino]pyrimidine trihydrochloride coated with a release-controlling film comprising a water-insoluble polymer film having no hydrophilic group.

2. The sustained-release formulation of 5-acetyl-4,6-dimethyl-2-[2-[4-(2-methoxyphenyl)piperazinyl]ethylamino]pyrimidine trihydrochloride according to claim 1, wherein the water-insoluble polymer film having no hydrophilic group is a copolymer of ethyl acrylate with methyl methacrylate.

3. The sustained-release formulation of 5-acetyl-4,6-dimethyl-2-[2-[4-(2-methoxyphenyl)piperazinyl]ethylamino]pyrimidine trihydrochloride according to claim 2, wherein the copolymer of ethyl acrylate with methyl methacrylate has a ratio of ethyl acrylate:methyl methacrylate=1 to 4:1.

4. The sustained-release formulation of 5-acetyl-4,6-dimethyl-2-[2-[4-(2-methoxyphenyl)piperazinyl]ethylamino]pyrimidine trihydrochloride according to claim 2, wherein the copolymer of ethyl acrylate with methyl methacrylate has a ratio of ethyl acrylate:methyl methacrylate=1.5 to 3.5:1.

5. The sustained-release formulation of 5-acetyl-4,6-dimethyl-2-[2-[4-(2-methoxyphenyl)piperazinyl]ethylamino]pyrimidine trihydrochloride according to claim 2, wherein the copolymer of ethyl acrylate with methyl methacrylate is an ethyl acrylate-methyl methacrylate copolymer emulsion.

* * * * *